United States Patent
Kobayashi et al.

(10) Patent No.: US 7,738,102 B2
(45) Date of Patent: Jun. 15, 2010

(54) LAYERED FILM FABRICATION METHOD, LAYERED FILM DEFECT DETECTION METHOD, LAYERED FILM DEFECT DETECTION DEVICE, LAYERED FILM, AND IMAGE DISPLAY DEVICE

(75) Inventors: Takamasa Kobayashi, Ibaraki (JP); Masaki Shikami, Ibaraki (JP); Yasuyuki Mikasa, Ibaraki (JP)

(73) Assignee: Nitto Denko Corporation, Ibaraki-shi, Osaka (JP)

( * ) Notice: Subject to any disclaimer, the term of this patent is extended or adjusted under 35 U.S.C. 154(b) by 190 days.

(21) Appl. No.: 12/160,150

(22) PCT Filed: Jan. 10, 2007

(86) PCT No.: PCT/JP2007/050119

§ 371 (c)(1),
(2), (4) Date: Jul. 7, 2008

(87) PCT Pub. No.: WO2007/080865

PCT Pub. Date: Jul. 19, 2007

(65) Prior Publication Data

US 2009/0009864 A1    Jan. 8, 2009

(30) Foreign Application Priority Data

Jan. 11, 2006  (JP)  .............................. 2006-003835
Dec. 14, 2006  (JP)  .............................. 2006-337127

(51) Int. Cl.
*G01N 21/00* (2006.01)
*G01J 4/00* (2006.01)

(52) U.S. Cl. ..................... 356/364; 356/389; 356/237.1; 356/239.1

(58) Field of Classification Search ......... 356/388–389, 356/237.1–237.5, 238.1–238.3, 239.1–239.8, 356/364–369, 429–431; 250/559.09, 559.42, 250/559.45, 559.46; 156/64, 378, 379
See application file for complete search history.

(56) References Cited

U.S. PATENT DOCUMENTS 5,640,244 A * 6/1997 Hellstrom et al. ........... 356/429

(Continued)

FOREIGN PATENT DOCUMENTS

CN    1249426 C    4/2006

(Continued)

OTHER PUBLICATIONS

International Search Report of PCT/JP2007/050119, date of mailing April 24, 2007.

(Continued)

*Primary Examiner*—Sang Nguyen
(74) *Attorney, Agent, or Firm*—Westerman, Hattori, Daniels & Adrian, LLP (57) ABSTRACT

Provided are a layered film defect detection device capable of performing defect detection considering irregularities of optical performance of a phase difference layer constituting the layered film without requiring insertion of a new part into an optical path; and a layered film defect detection method. A defect detection device used for a layered film (11) having a polarizing plate (1) and a phase difference layer (separator (2)) includes: a light source (12) arranged at one side of the film surfaces of the layered film (11), an imaging unit (13) arranged on the other side of the film surface; an inspection polarization filter (15) arranged between the light source (12) and the imaging unit (13); a defect detection unit (14b) for detecting a defect existing on the polarizing plate (1) according to the captured image; and an optical axis adjusting unit (16) for adjusting a relative angle position of the polarization axis (L2) of a polarizing filter (15) and a polarization axis (L1) of a polarizer (2). In the detection device, the relative angle position of the polarizing filter (15) is adjusted within a range of the polarization axis angle x of the polarizing filter satisfying the relationship 0 degrees<xf 15 degrees so as to minimize the visible light quantity inputted to the imaging unit.

9 Claims, 7 Drawing Sheets

U.S. PATENT DOCUMENTS

| | | | |
|---|---|---|---|
| 5,666,199 A * | 9/1997 | Hess et al. | 356/364 |
| 5,734,158 A | 3/1998 | Nagashima et al. | |
| 6,034,754 A * | 3/2000 | Sato et al. | 349/102 |
| 6,636,322 B1 * | 10/2003 | Terashita | 356/492 |
| 7,006,224 B2 * | 2/2006 | Some | 356/369 |
| 7,407,822 B2 * | 8/2008 | Kato et al. | 438/16 |
| 7,499,162 B2 * | 3/2009 | Shibata et al. | 356/369 |
| 7,593,106 B2 * | 9/2009 | Hellstrom | 356/430 |
| 2009/0288754 A1 * | 11/2009 | Kobayashi et al. | 156/64 |

FOREIGN PATENT DOCUMENTS

| | | | |
|---|---|---|---|
| JP | 08114432 A * | 5/1996 | |
| JP | 8-292406 A | 11/1996 | |
| JP | 10-311777 A | 11/1998 | |
| JP | 2004-170495 A | 6/2004 | |
| JP | 2005-9919 A | 1/2005 | |
| JP | 2005-351825 A | 12/2005 | |
| KR | 10-2004-0044071 A | 5/2004 | |

OTHER PUBLICATIONS

Notification of Transmittal of Copies of Translation of the International Preliminary Report on Patentability (Form PCT/IB/338) of International Application No. PCT/JP2007/050119 mailed Jul. 24, 2008 with Forms PCT/IB/373, PCT/IB/326, PCT/ISA/237 and English translation of PCT/ISA/237.

* cited by examiner

FIG. 10 ical field, a layered film defect detection method, a layered film defect detection device, a layered film, and an image display device.
LAYERED FILM FABRICATION METHOD, LAYERED FILM DEFECT DETECTION METHOD, LAYERED FILM DEFECT DETECTION DEVICE, LAYERED FILM, AND IMAGE DISPLAY DEVICE

TECHNICAL FIELD

The present invention relates to a fabrication method of a layered film in which a polarizing plate and a retardation layer having large orientation angle variation in plane are layered, a layered film defect detection method, a layered film defect detection device, a layered film, and an image display device.

BACKGROUND ART

Figure 10:
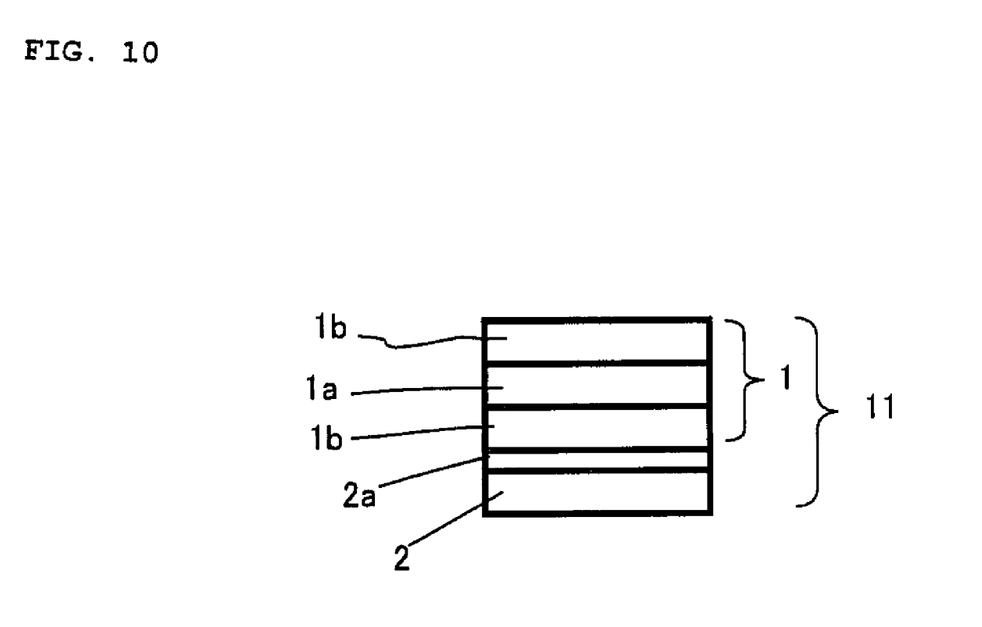
FIG. 10 is a view showing a cross sectional configuration of a layered film.

A layered structure shown in FIG. 10 is known for such layered film. A layered film 11 is configured by a polarizing plate 1 including a protective film 1b layered on both sides of a polarizer 1a via an adhesive layer, and a separator 2 layered on one side of the polarizing plate 1 via an adhesive layer 2a. When inspecting defects such as foreign substances, scratches, nicks and the like existing on the polarizing plate 1, light is irradiated from an appropriate light source onto the polarizing plate 1, a reflected light image or a transmitted light image is acquired via an imaging unit such as a line sensor or a two-dimensional TV camera, and defect detection is performed based on the acquired image data. When inspecting the polarizing plate 1, the image data is acquired with an inspection polarization filter interposed in a light path between the light source and the imaging unit. Normally, a polarizing axis (e.g., polarized absorption axis) of an inspection polarization filter is arranged in a state (cross Nicol) orthogonal to a polarizing axis (e.g., polarized absorption axis) of the polarizing plate 1 to be inspected. According to the cross Nicol arrangement, an all-black image is input from the imaging unit if defect is absent, and the corresponding portion does not become black if the defect is present. Therefore, defect can be detected by setting an appropriate threshold value.

However, in the case of a layered film in which the polarizing plate 1 includes the separator 2, the linear polarized light is converted to an elliptical polarized light since the separator 2 has a birefringence (retardation), and the polarizing plate 1 and the inspection polarization filter substantially will not be in a cross Nicol state. As a result, the defect inspection of the polarizing plate 1 in the layered film 11 cannot be accurately performed.

A polarizing plate inspection device disclosed in Patent Document 1 is known as a layered film defect detection device resolved with the above problem. The polarizing plate inspection device includes a light source and an inspection polarization filter for converting the light from the light source to a linear polarized light, wherein the linear polarized light is entered to a polarizing plate with protective film (corresponding to retardation layer), and defect detection is performed based on the transmitted light image. Furthermore, a retardation plate for compensating the birefringence of the light caused by the protective film is arranged on the light path transmitting through the polarizing plate with protective film from the light source. The phase change by the protective film is canceled and the birefringence of the light by the protective film is compensated by separately arranging the retardation plate. Moreover, a configuration example of arranging a variable polarization optical element in which the phase angle of light can be adjusted by voltage to compensate the birefringence by the protective film that slightly differs for every product is disclosed.

Patent Document 1: Japanese Laid-Open Patent Publication No. 2005-9919

DISCLOSURE OF THE INVENTION

Problems to be Solved by the Invention

However, since the retardation plate for inspection and variable polarization optical element need to be separately arranged in Patent Document 1, excess component increases, the light quantity of the light source lowers due to interposition of the excessive component, and the inspection accuracy lowers, and thus high accuracy and high quality inspection requirement that is being demanded on recent polarizing plate cannot be withstood. Furthermore, if the retardation layer configuring the layered film 11 is a temporarily attached film that is stripped when used for the last time such as the separator, such film is a film in which the in-plane retardation or the orientation angle of the molecule does not need to be strictly controlled, whereby the orientation angle variation in film surface and for every product lot becomes relatively large, and the retardation cannot be completely canceled even if a specific retardation plate for inspection as described in patent document 1 is used, and the inspection accuracy cannot be enhanced.

The relevant retardation layer not only converts the linear polarized light to elliptical polarized light, but also the polarized state differs between the central part and the edges of the image due to the variation described above, and the image to be input to the imaging unit differs in brightness between the central part and the ends. The contrast between the defect part and the other image parts is ideally constant regardless of the location in the image, but the contrast becomes uneven due to the above reasons. As a result, determination might be made as pass although there is a luminescent point such as pin hole that is apparently large, and on the other hand, erroneous determination might be made as fail although the defect is a very small defect that should be determined as pass. For instance, in FIG. 8, the defect on the left side can be relatively easy to detect, but detection leakage tends to easily occur for the defect on the right side since the display around the defect becomes too bright. That is, the defect detection ability needs to be constant between the central part and the ends of the image. Therefore, defect inspection that takes variation into consideration cannot be performed by simply inserting the retardation plate as in Patent Document 1.

In view of the above problems, the present invention aims to provide a layered film fabrication method capable of performing defect detection taking variation of optical performance of the retardation layer configuring the layered film into consideration without inserting a new component into the light path, a layered film defect detection method, a layered film defect detection device, a layered film, and an image display device.

Means for Solving the Problems

In order to solve the above problems, a fabrication method of a layered film according to the present invention relates to a layered film fabrication method including the steps of fabricating a layered film by layering at least a polarizing plate and a retardation layer, and performing defect inspection of the fabricated layered film, wherein the defect inspection step includes the steps of irradiating a light on the layered film from a light source arranged on one side of a film surface of the layered film, imaging a transmitted light image of the layered film by an imaging unit arranged on the other side of the film surface, detecting a defect existing in the layered film based on the transmitted light image imaged by the imaging unit, and adjusting a relative angle position of a polarizing axis of an inspection polarization filter arranged on a light path between the film surface and the imaging unit and a polarizing axis of the polarizing plate, and the relative angle position adjustment of the polarization filter includes adjusting a relative angle position x of the polarization filter in a range of $0°{\leq}x{\leq}15°$ so that a light quantity of a visible light entered to the imaging unit becomes a minimum value.

Furthermore, in order to solve the above problems, a layered film defect detection method relates to a defect detection method of a layered film in which at least a polarizing plate and a retardation layer are layered, the method including the steps of irradiating a light on the layered film from a light source arranged on one side of a film surface of the layered film, imaging a transmitted light image of the layered film by an imaging unit arranged on the other side of the film surface, detecting a defect existing in the layered film based on the transmitted light image imaged by the imaging unit, and adjusting a relative angle position of a polarizing axis of an inspection polarization filter arranged on a light path between the film surface and the imaging unit and a polarizing axis of the polarizing plate, wherein the relative angle position adjustment of the polarization filter includes adjusting a relative angle position x of the polarization filter in a range of $0°{\leq}x{\leq}15°$ so that a light quantity of a visible light entered to the imaging unit becomes a minimum value.

The effects of the layered film fabrication method and the defect detection method of the above configuration will be described. The layered film to be inspected has at least the polarizing plate and the retardation layer layered. The light source is arranged on one side of the film surface of the layered film, and the imaging unit (e.g., line sensor camera) is arranged on the other side. The inspection polarization filter is arranged in the light path between the light source and the imaging unit. The inspection polarization filter may be arranged on one or the other side of the film surface, but is preferably arranged on the imaging unit side since degradation of the polarization filter due to heat and light of the light source or reduction in light quantity does not occur, and it may be relatively small. The light irradiated from the light source has only the linear polarized light passed through the normal portion and the lights other than the linear polarized light transmitted through the defect portion when being transmitted through the layered film to be inspected, and thus the light passed through the polarization film has the portion without defect displayed in black and the defect portion displayed brighter, and the transmitted light image of the layered film is input to the imaging unit. The defect detection unit performs defect detection based on the image data of the input transmitted light image. Numerous techniques and algorithms are known for performing defect detection, and are not limited to a specific detection method.

In the present invention, a function of adjusting the relative angle position of the polarizing axis of the inspection polarization filter and the polarizing axis of a polarizer is provided. This is because an optimum relative angle position can be set in view of the retardation and the orientation angle variation by the retardation layer, as described above. Specifically, assuming the position at which the polarizing axes of the polarizing plate and the inspection polarization filter are orthogonal is a reference (0°) of the relative angle position, the relative angle position x of the polarization filter is rotated in a plane orthogonal to the rotation axis within a range of $0°{<}x{\leq}15°$ to be set at a position where the light quantity becomes a minimum. The light quantity to be input to the imaging unit thereby becomes substantially constant in the surface of the layered film to be inspected, and defect detection of satisfactory accuracy can be performed. If the relative angle position of the polarization filter becomes too large, the light quantity to be input to the imaging unit becomes too large, and defect detection becomes difficult. The relative angle position is appropriately set in a range from the reference position 0° to ±15° depending on the retardation and the orientation angle of the retardation layer. As a result, defect detection that takes variation in optical performance of the retardation layer configuring the layered film can be performed without inserting a new component such as a retardation film into the light path. In particular, the relevant effects are greatly exhibited when the orientation angle variation is large.

A layered film fabrication method according to the present invention includes the steps of fabricating a layered film by layering at least a polarizing plate and a retardation layer, and performing defect inspection of the layered film, wherein the defect inspection step can perform defect detection taking variation in optical performance of the retardation layer configuring the layered film without inserting a new component such as a retardation film into the light path, as described above.

Moreover, in order to solve the above problems, a layered film defect detection device according to the present invention relates to a defect detection device of a layered film in which at least a polarizing plate and a retardation layer are layered, the device including a light source arranged on one side of a film surface of the layered film and irradiating a light on the layered film, an imaging unit arranged on the other side of the film surface and imaging a transmitted light image of the layered film, an inspection polarization filter arranged on a light path between the film surface and the imaging unit, a defect detection unit for detecting a defect existing in the layered film based on the transmitted light image imaged by the imaging unit, and an optical axis adjustment unit for adjusting a relative angle position of a polarizing axis of the polarization filter and a polarizing axis of the polarizing plate, wherein the optical axis adjustment unit adjusts a relative angle position x of the polarization filter in a range of $0°{\leq}x{\leq}15°$ so that a light quantity of a visible light entered to the imaging unit becomes a minimum value.

According to the relevant defect detection device, defect detection taking variation in optical performance of the retardation layer configuring the layered film into consideration is performed without inserting a new component such as a retardation film into the light path, as described above.

In the present invention, the optical axis adjustment unit preferably adjusts the relative angle position by rotating the polarization filter. The optimum relative angle position can be searched by rotating the polarization filter, and the inspection polarization filter can be arranged at an appropriate position with respect to each type of product by rotating the polarization film even if the type of layered film is different.

In the present invention, the optical axis adjustment unit preferably has one polarization filter selected from a plurality of polarization filters having a polarizing axis set in different directions arranged on the light path. The optimum polarization filter can be arranged in the light path by selecting one of the plurality of polarization filters having the polarizing axis set in different directions instead of rotating the polarization filter in plane.

DESCRIPTION OF SYMBOLS 1 polarizing plate
1a polarizer
1b protective film
2 separator
11 layered film
12 imaging unit
13 light source
14 image processing device
14a light quantity detection unit
14b defect detection unit
15 inspection polarization filter
16 optical axis adjustment unit
17 image data acquiring unit
18 monitor
19 storage device
20 marking device
21 marking control unit
L1, L2 polarizing axis

BEST MODE FOR CARRYING OUT THE INVENTION

One example of a suitable embodiment of layered film defect detection method and device according to the present invention will now be described with reference to the figures.

Figure 1:
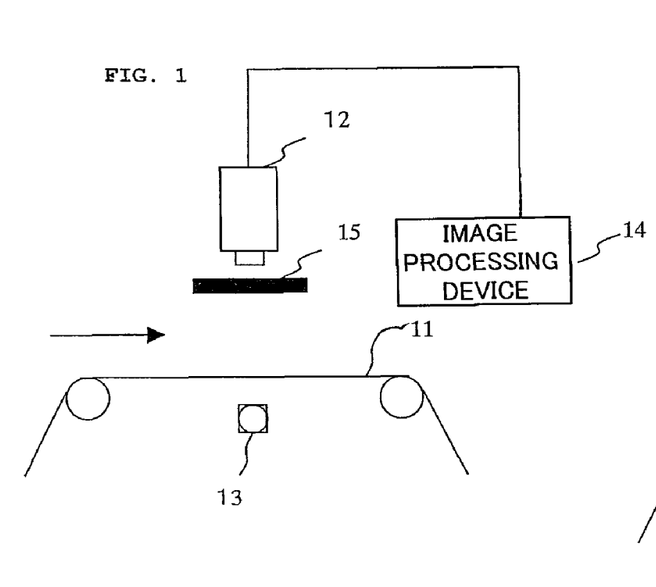
FIG. 1 is a schematic view showing a configuration of a layered film defect detection device.

FIG. 1 is a schematic view showing a configuration of the defect detection method and device. A layered film 11 to be inspected has a layered configuration as shown in FIG. 10, wherein a separator 2 (corresponding to retardation layer) is layered on one side of a polarizing plate 1. The cross sectional structure of the layered film 11 is however not limited thereto, and may have a structure in which a surface protective film is further layered.

In FIG. 1, the polarizing plate 1 configuring the layered film 11 is pulled out from a state wound to a roll (not shown), and conveyed from the left side to the right side of the figure. A light source 13 for inspection is arranged on one side (lower side in FIG. 1) of a film surface of the layered film 11. The light source 13 may be fluorescent lamp, halogen lamp, metal halide lamp, LED, or the like, and the appropriate light source 13 is selected depending on the type of layered film 11 (polarizing plate 1) to be inspected. Planar shape, light bulb shape, rectangular shape in the film width direction, and the like may be appropriately adopted for the shape of the light source 13.

Figure 2:
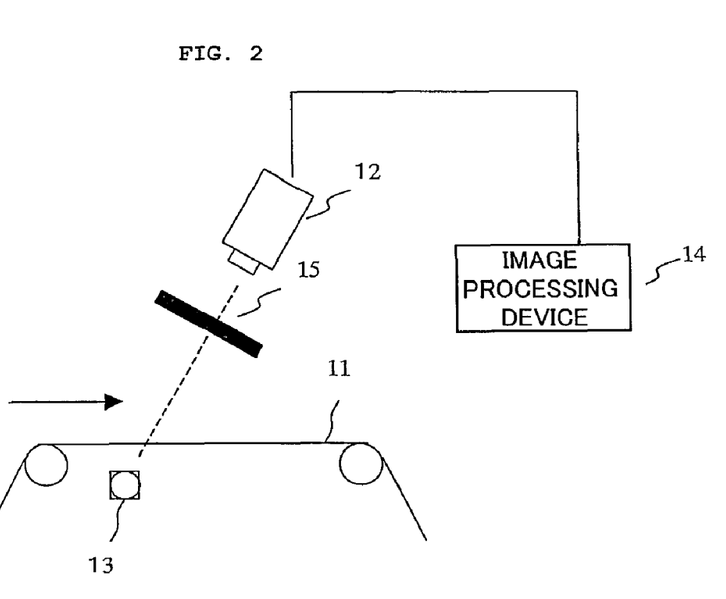
FIG. 2 is a schematic view showing another configuration of a layered film defect detection device.

An imaging unit 12 is configured by a line sensor camera, a two-dimensional TV camera, or the like. One or a plurality of imaging units 12 is arranged along the width direction depending on the size in the width direction of the layered film 11. An image processing device 14 has a function of performing defect detection of the layered film 11 (polarizing plate 1) by performing image processing on the image data imaged by the imaging unit 12. A light path connecting the imaging unit 12 and the light source 13 is set to be perpendicular to the film surface of the layered film 11, but the light path may be inclined with respect to the film surface as shown in FIG. 2 due to the restriction in installing locations of the light source 13 and the imaging unit 12.

As shown in FIG. 1, an inspection polarization filter 15 is arranged on the front surface of the imaging unit 12. A polarizing axis L2 (see FIG. 3) of the inspection polarization filter 15 is normally arranged to be in a cross Nicol position relationship with a polarizing axis L1 of the polarizing plate 1, but is substantially not in a cross Nicol relationship due to the presence of the separator 2 (retardation layer) as described above. Such retardation layer also has a property that the variation of the orientation angle is large. Therefore, it is not appropriate in terms of inspection accuracy to arrange the inspection polarization filter 15 in cross Nicol, and the inspection polarization filter 15 needs to be arranged at an optimum position in view of the properties of the retardation layer. The inspection polarization filter 15 used is similar to the polarizing plate 1 and is defect-free.

Figure 3:
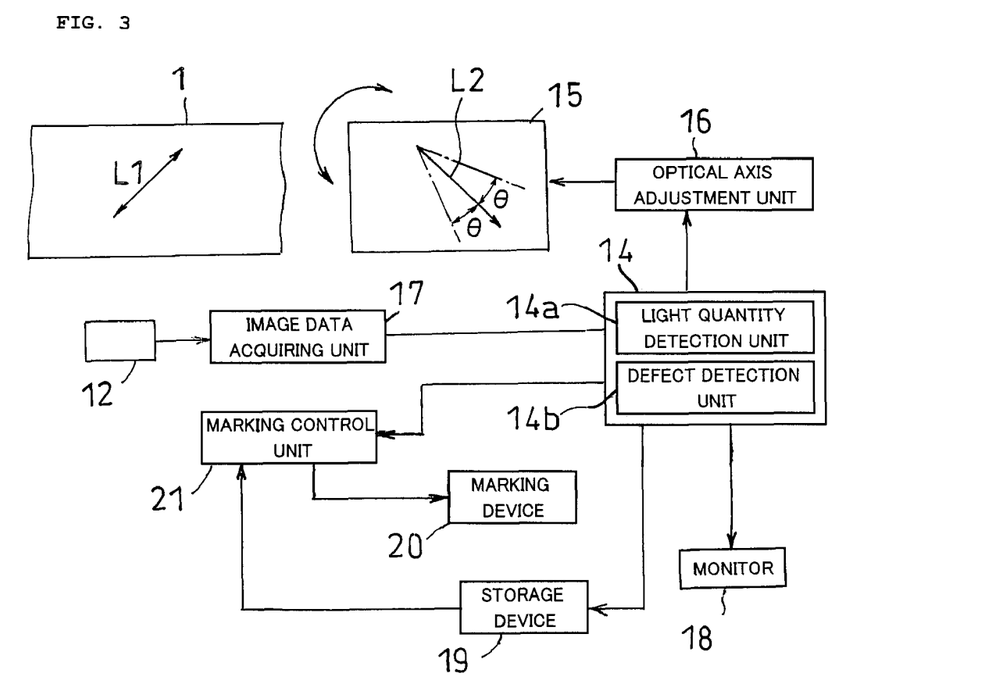
FIG. 3 is a view illustrating an adjustment mechanism of a polarizing axis of an inspection polarization filter.

FIG. 3 is a view illustrating adjustment of the polarizing axis L2 of the inspection polarization filter 15. An optical axis adjustment unit 16 provides a mechanism for rotating the inspection polarization filter 15 in plane. The center of rotation coincides with the light path connecting the light source 13 and the imaging unit 12.

Since there are various types of layered film 11 to be inspected, the optimum arrangement of the inspection polarization filter 15 differs depending on the type of the layered film 11. Appropriate defect detection can be performed depending on the type of the layered film 11 by arranging the mechanism for horizontally rotating the inspection polarization filter 15 as shown in FIG. 3. In this case, it is preferable to stamp or print the rotation angle, or attach a mark to the inspection polarization filter 15 to know how many times the inspection polarization filter 15 has been rotated with respect to the reference position. A relationship between the type of the polarizing plate 1 and the angle position may be stored in a memory to enable automatic setting to a predetermined angle position by the optical axis adjustment unit 16.

An image signal imaged by the imaging unit 12 is converted to image data digitalized by an image data acquiring unit 17, and sent to an image processing device 14. The image processing device 14 is configured with the software function as the core, and has a function of a light quantity detection unit 14a and a defect detection unit 14b. The light quantity detection unit 14a detects the position where the brightness of the imaged image becomes a minimum. The defect detection unit 14b performs defect detection by image processing the image data acquired by the imaging unit 12, wherein a known method is used for the defect detection algorithm. For instance, since the luminance of the location where the defect exists becomes bright, defect can be extracted by binarizing the acquired image data with a threshold value of a predetermined level. The feature quantity such as area, length, width, and luminance of the extracted defect are calculated, and one or a plurality of the feature quantity is selected to determine a pass/fail.

A monitor 18 can project the image imaged by the imaging unit 12 to visually check the presence of the defect. A storage device 19 stores position coordinate, feature quantity of the defect, and the like when the defect is detected. A marking device 20 is a device for marking the defect position when the defect is extracted. A marking control unit 21 controls the operation of the marking device 20. Specifically, the marking device 20 is controlled so that the defect position (or end in the width direction of the polarizing plate 1) is accurately marked based on the coordinate signal of the defect position stored in the storage device 19. A device having a known configuration may be used for the marking device 20. The marking may be performed with a magic marker. The feature quantity (defect information) of the defect may be printed on the polarizing plate 1 with an inkjet printer and the like.

Figure 5:
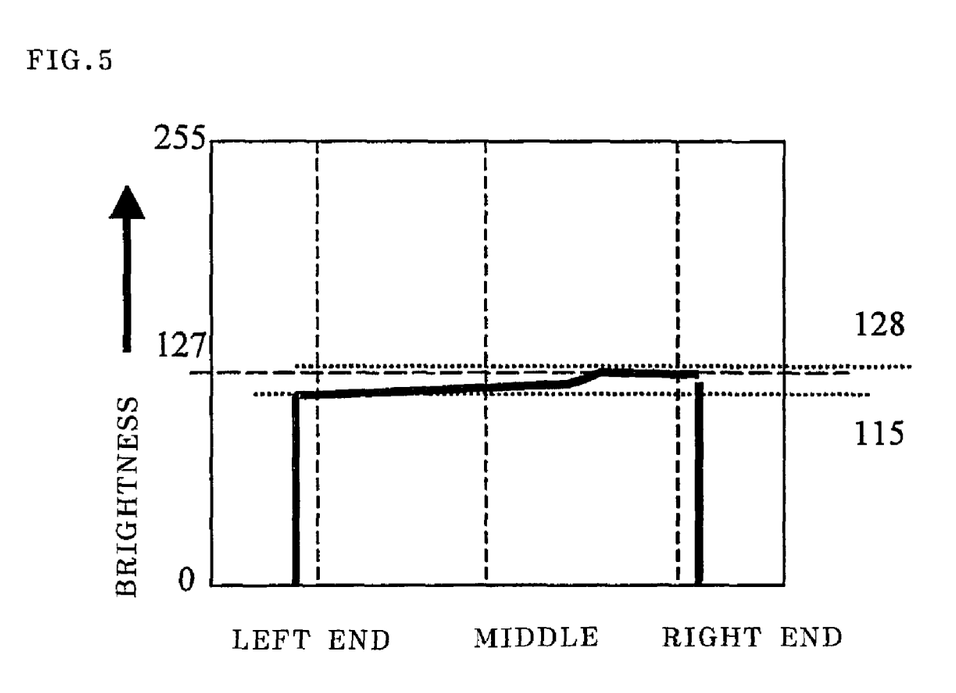
FIG. 5 is a view showing an image signal imaged while rotating a polarization filter to a position at which the light quantity becomes a minimum with respect to a polarizing plate including a retardation layer.
Figure 8:
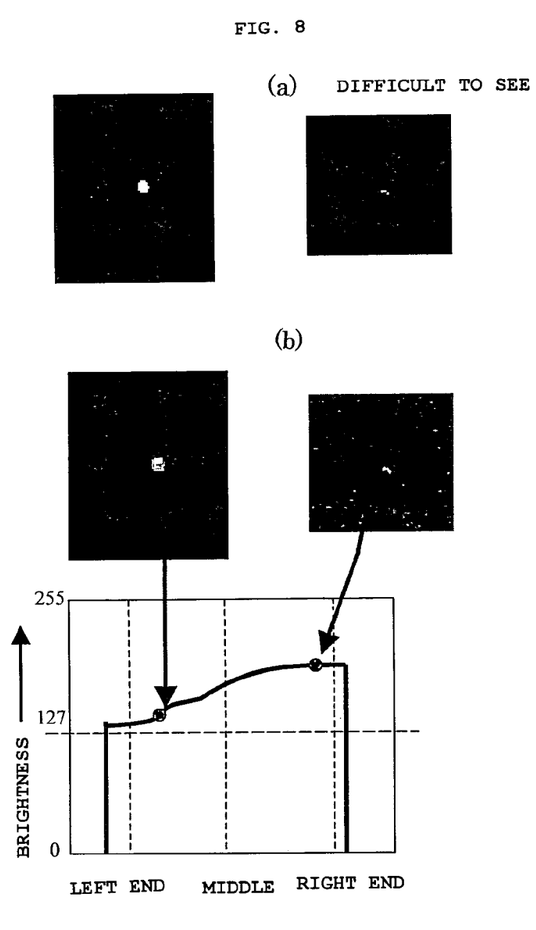
FIG. 8 is a view showing an original image and a binary image in the example of FIG. 6.
Figure 9:
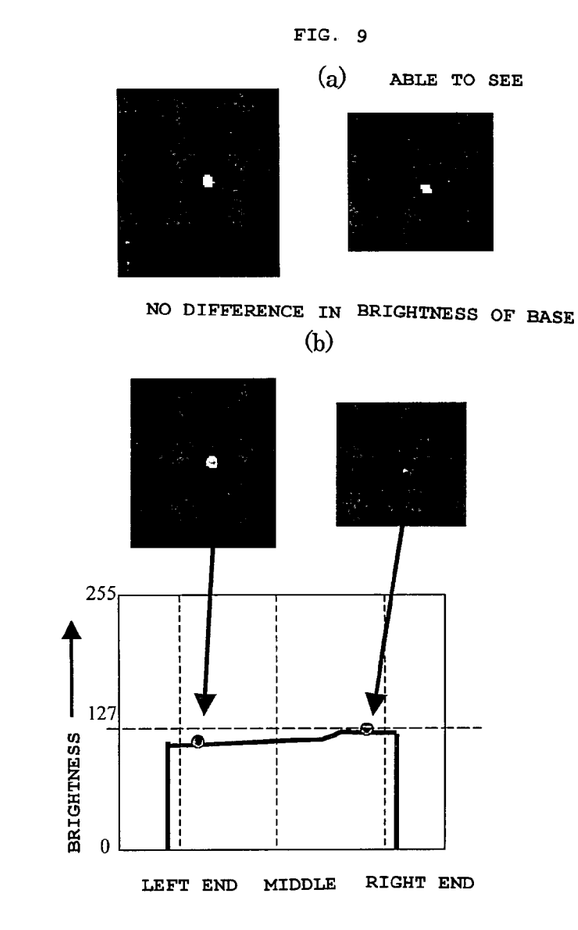
FIG. 9 is a view showing an original image and a binary image in the example of FIG. 5.

The arrangement of the inspection polarization filter 15 will now be described. First, the inspection polarization filter 15 is set at a position that becomes cross Nicol with the polarizing plate 1 in the layered film 11 to be inspected (reference position=0°). This state is a state having a defect that is difficult to detect as shown in FIG. 8. The polarization filter 15 is then rotated to a position at which the light quantity becomes a minimum value while checking the data (e.g., FIG. 6) input by the imaging unit 13 and processed by the light quantity detection unit 14a. The light quantity to be output thus becomes substantially constant in the film surface as shown in FIG. 5, and the defect that was difficult to detect as shown in FIG. 9 now can be easily detected. Having the light quantity to be output substantially constant includes having the difference between the maximum value and the minimum value of brightness to smaller than or equal to 40, which difference is preferably smaller than or equal to 25 to raise the detection accuracy, and more preferably smaller than or equal to 15 if the brightness is divided into 256 tones (e.g., black display=0, white display=255). The setting of the polarization filter 15 can be automated, wherein the light quantity detection unit 14a and the optical axis adjustment unit 16 are provided as shown in FIG. 3, and a mechanism automatically set to a position at which the light quantity becomes a minimum value via a computer is provided. Such automated mechanism enables inspection in an optimum state depending on the state of the continuously conveyed layered film, and thus is preferably used in continuous production and inspection.

Figure 4:
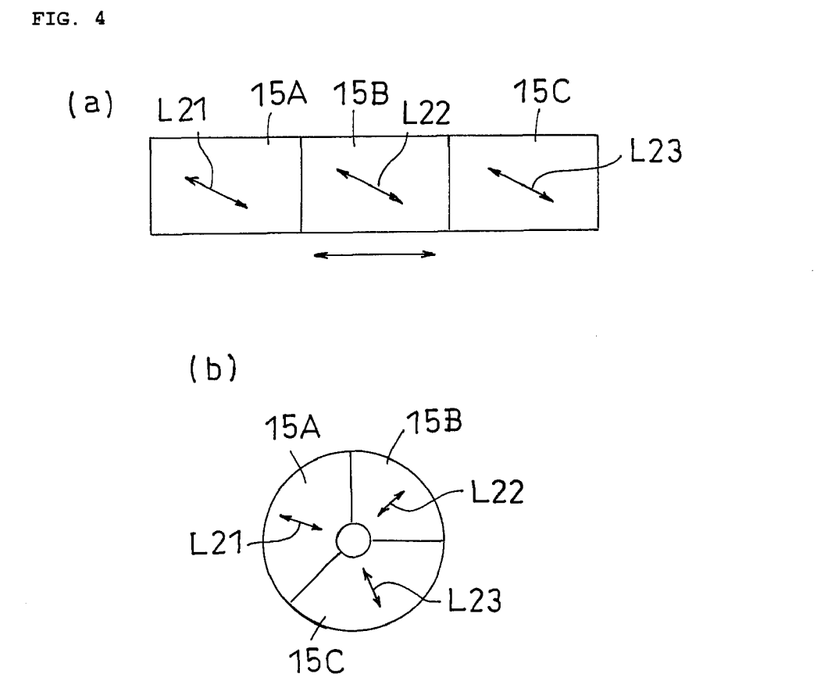
FIG. 4 is a view illustrating another embodiment of an adjustment mechanism of a polarizing axis of an inspection polarization filter.

FIG. 4 is a view showing another embodiment of the inspection polarization filter 15. FIG. 4(a) shows three inspection polarization filters 15A, 15B, and 15C having different polarizing axes connected in a line, wherein the relative angle position of the polarizing axes can be adjusted by arranging one of the polarization filters 15 on the light path. The polarizing axes L21, L22, L23 of the respective inspection polarization filters 15A, 15B, 15C differ slightly from each other. FIG. 4(b) shows three polarization filters 15A, 15B, 15C having different polarizing axes connected in a circumferential direction. In the example of FIG. 4, the number of polarization filter 15 is three, but is not limited thereto, and can be appropriately determined.

A specific example will be described by way of example. A halogen lamp is used as the light source 13, and a line sensor camera is used as the imaging unit 12. The layered film 11 to be inspected includes a separator (Cerapeel MDA38 manufactured by Toray Advanced Film Co., orientation angle variation of 8.6°) serving as the retardation layer and is defect-free. The light quantity is monitored while rotating the inspection polarization filter 15, and the image signal obtained by the imaging unit 12 at a position (relative axis angle of the polarization filter is 5°) at which the light quantity becomes a minimum value is shown in FIG. 5. Although slight fluctuation is found between the central part and the ends of the image, the luminance in the field view direction (main scanning direction) of the line sensor camera is substantially constant, and a stable inspection can be performed regardless of at which position the defect is located.

The light source 13 used in verification is halogen light source device MHF-100 (100 Watts) manufactured by Moritex Co., wherein the brightness of the light source (brightness of measurement at 30 cm above the light source) is adjusted to be 6060 cd/m².

Figure 6:
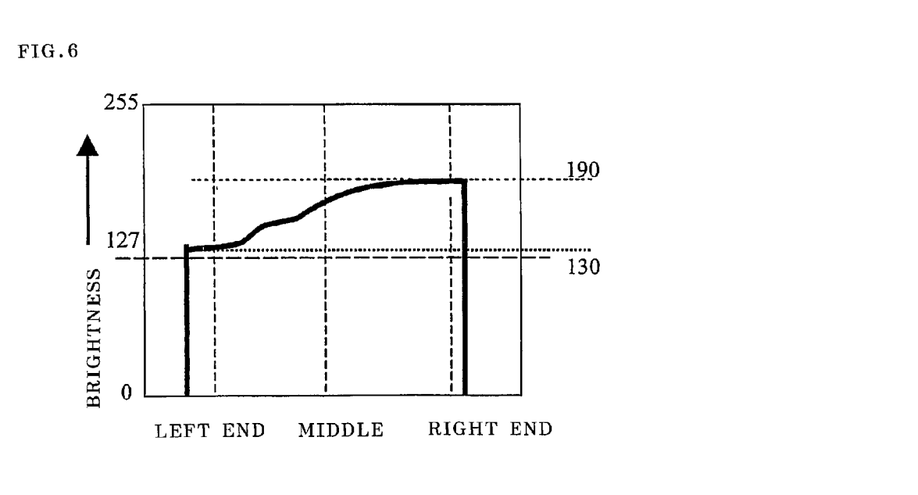
FIG. 6 is a view showing an image signal when imaged using a polarization filter arranged in cross Nicol with respect to a polarizing plate including a retardation layer.

The image signal shown in FIG. 6 is obtained by imaging the case when the inspection polarization filter 15 is arranged so as to be cross Nicol (relative axis angle of polarization filter is 0°) in using the polarizing plate 1 in which the retardation layer is not layered, and thereafter, the polarizing plate in which the retardation layer is not layered is replaced with the polarizing plate 1 in which the retardation layer is layered. If arranged in cross Nicol when the retardation layer is arranged, the pass/fail of defect cannot be stably determined since the difference in luminance is large and unstable between the central part and the ends.

Figure 7:
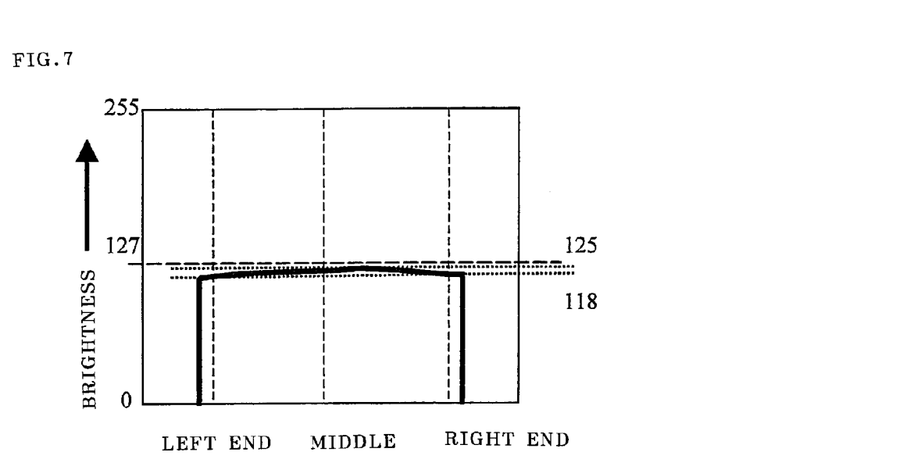
FIG. 7 is a view showing an image signal when imaged using a polarization filter arranged in cross Nicol with respect to a polarizing plate not including a retardation layer.

The image signal in the case when the inspection polarization filter 15 is arranged in cross Nicol while using the polarizing plate 1 in which the retardation layer is not layered and the defect does not exist is shown in FIG. 7.

The area (pixel unit) of the defect in the case when the defect which area at the position of the central part of FIG. 7 is detected as "20" is detected at the positions on the left end, middle, and right end under the conditions of FIGS. 5 to 7 is shown in table 1. Inspector manufactured by Matrox Co. is used to calculate the area. In FIGS. 5 to 7, the maximum value, the minimum value, and the difference between the maximum value and the minimum value in the case when the brightness is represented in 256 tones are shown in table 2. The numerical values in table 2 indicate the values detected with the method similar to table 1.

Figure 5A:
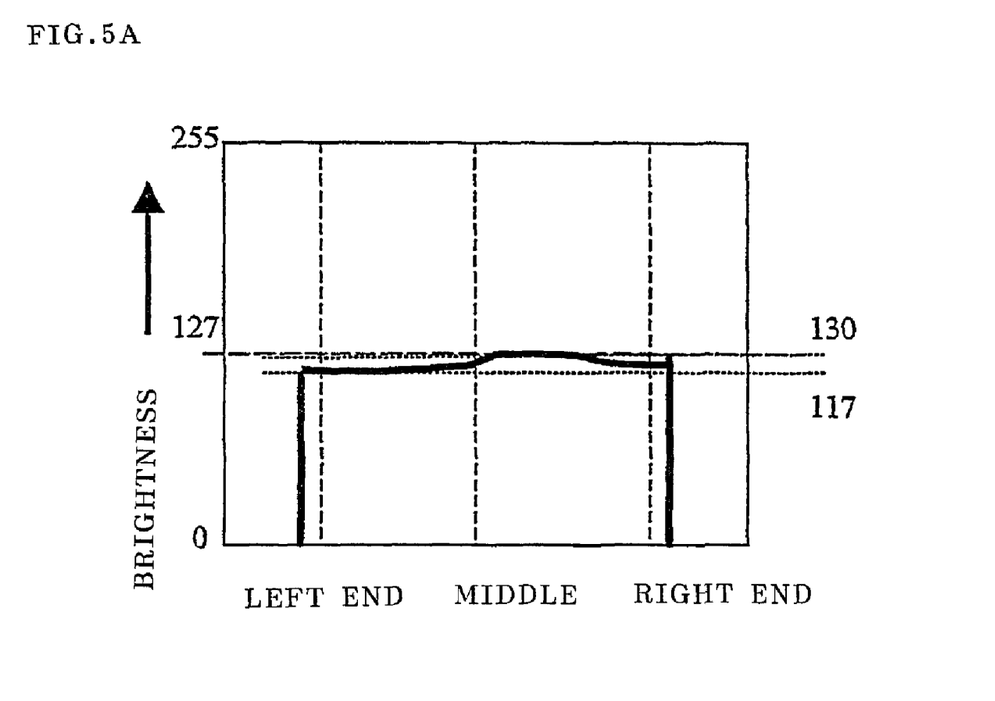
FIG. 5A is a view showing an image signal imaged while rotating a polarization filter to a position at which the light quantity becomes a minimum with respect to a polarizing plate including a retardation layer.
Figure 5B:
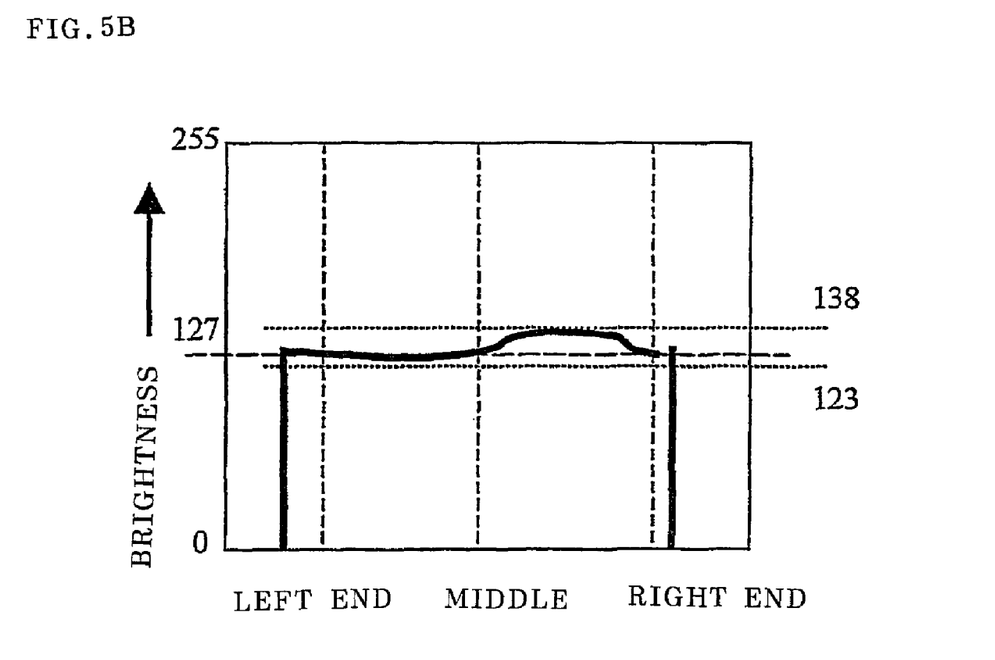
FIG. 5B is a view showing an image signal imaged while rotating a polarization filter to a position at which the light quantity becomes a minimum with respect to a polarizing plate including a retardation layer.
Figure 5C:
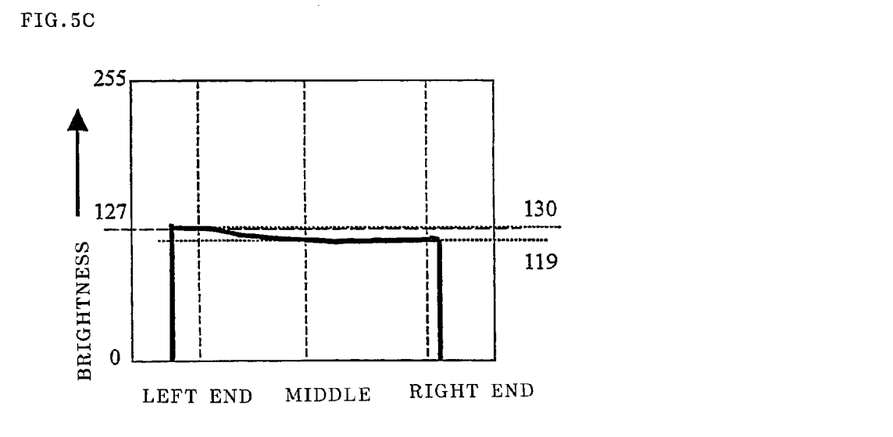
FIG. 5C is a view showing an image signal imaged while rotating a polarization filter to a position at which the light quantity becomes a minimum with respect to a polarizing plate including a retardation layer.

FIG. 5A shows the image signal in the case when the separator having orientation angle variation of 8.11° is used instead of the separator used in FIG. 5. The relative axis angle of the polarization filter 15 is 7°. FIG. 5B shows the image signal in the case when the separator having orientation angle variation of 7.35° is used instead of the separator used in FIG. 5. The relative axis angle of the polarization filter 15 is 9°. FIG. 5C shows the image signal in the case when the separator having orientation angle variation of 7.93° is used instead of the separator used in FIG. 5. The relative axis angle of the polarization filter 15 is 6°. Such separators all use Cerapeel MDA 38 manufactured by Toray Advanced Film Co. The adjustment angle of the inspection polarization filter 15 is within 15° in all the separators.

TABLE 1

|  | FIG. 5 | FIG. 6 | FIG. 7 |
|---|---|---|---|
| Left end | 21 | 14 | 21 |
| Middle | 19 | 7 | 20 |
| Right end | 16 | 2 | 21 |

TABLE 2

|  | FIG. 5 | FIG. 5A | FIG. 5B | FIG. 5C | FIG. 6 | FIG. 7 |
|---|---|---|---|---|---|---|
| Maximum | 128 | 130 | 138 | 130 | 190 | 125 |
| Minimum | 115 | 117 | 123 | 119 | 130 | 118 |
| Difference | 13 | 13 | 15 | 11 | 60 | 7 |

In the case of FIG. 5 or FIG. 7, the area is substantially the same size regardless of at which position the defect is located, but in the case of FIG. 6, the area differs greatly depending on the position, and stable defect detection cannot be performed. The actual image in the case of FIG. 6 is shown in FIG. 8. FIG. 8(a) is a binary image, and (b) shows an original image before binarization. The luminance of the background of the defect differs depending on the inspecting position, wherein the size of the defect on the right side is detected smaller than the actual size.

The actual image in the case of FIG. 5 is similarly shown in FIG. 9. In this case, the detection accuracy is the same for the central part and the ends since there is no difference in luminance of the background by the inspecting position, and the area of defect at any position is correctly detected unlike to FIG. 8.

<Specific Example of Layered Film>

The layered film 11 including the polarizing plate 1 has been described as an example of the present invention, and a specific configuration example will be further described below. The polarizing plate is formed to a long band shape, and the polarizing plate of respective size is obtained by being punched out from a polarizing plate original fabric of film shape. The polarizing plate original fabric is obtained by laminating a TAC film (protective film) etc. on both front and back sides of the PVA film (polarizer) fabricated in advance. The defect (scratches, foreign substances, etc.) on the surface or on the inside of the polarizing plate original fabric N having a multi-layered structure needs to be detected.

The polarizing plate original fabric N is fabricated with a fabrication method including (A) step of drying a polyvinyl alcohol film subjected to dying, crosslinking and stretching processes, and obtaining a polarizer; (B) step of laminating a protective layer on one side or on both sides of the polarizer; and (C) step of performing heating process after laminating.

The respective processes of dying, crosslinking, and stretching of the polyvinyl alcohol film do not need to be separately performed and may be simultaneously performed, or the order of each process may be arbitrary. The polyvinyl alcohol film subjected to swelling process may be used for the polyvinyl alcohol film. Generally, the polyvinyl alcohol film is immersed in a solution containing iodine and dichroic dye to be dyed by attracting the iodine and the dichroic dye, and then washed, uniaxially stretched to a stretching magnification of three to seven times in a solution containing boric acid and pyroborate, and then dried. After stretching in the solution containing iodine and dichroic dye, the film is further stretched (two-stage stretching) in the solution containing boric acid and pyroborate, and thereafter dried, so that the orientation of iodine enhances and polarization degree improves, and thus it is particularly preferable.

The polyvinyl alcohol polymer includes those saponified after polymerizing vinyl acetate, those in which a small amount of copolymerizable monomers such as unsaturated carboxylic acid, unsaturated sulfonic acid, cation monomer etc. is copolymerized to the vinyl acetate, and the like. The average polymerization degree of the polyvinyl alcohol polymer is not particularly limited and may be an arbitrary value, but is preferably greater than or equal to 1000, and more preferably between 2000 and 5000. The saponification degree of the polyvinyl alcohol polymer is preferably greater than or equal to 85 mol % and more preferably between 98 and 100 mol %.

The thickness of the polarizer to be fabricated is generally between 5 and 80 µm, but is not limited thereto, and the method for adjusting the thickness of the polarizer is not particularly limited, wherein usual methods using tenter, roll stretching, rolling etc. may be used.

An adhering process of the polarizer and the polarizer protective film or the protective layer is not particularly limited, but is performed by way of adhesive including vinyl alcohol polymer, adhesive including at least water-soluble crosslinking agent of vinyl alcohol polymer such as boric acid and pyroborate, glutaraldehyde and melamine, oxalic acid, and the like, etc. The adhesive layer is formed as an applied dry layer etc. of aqueous solution, but other additives and catalysts such as acid can also be optionally compounded in preparing the aqueous solution.

An appropriate transparent film can be used for the polarizer protective film arranged on one side or both sides of the polarizer. Among them, a film made of polymer excellent in transparency, mechanical strength, heat stability, moisture shielding property, and the like is preferably used. The polymer includes acetate resin such as triacetyl cellulose, polycarbonate resin, polarylate, polyester resin such as polyethylene telephtalate, polyimide resin, polysulfone resin, polyether sulfone resin, polystylene resin, polyethylene, polyolefin resin such as polypropylene, polyvinyl alcohol resin, polyvinyl chloride resin, polynorbornene resin, polymethyl methacrylate resin, liquid crystal polymer, and the like. The film may be fabricated with any one of casting method, calendar method, and extrusion method.

The polymer film disclosed in Japanese Laid-Open Patent Publication No. 2001-343529 (WO01/37007), such as resin composition containing (A) thermoplastic resin having substituted and/or unsubstituted imide group on the side chain, and (B) thermoplastic resin having substituted and/unsubstituted phenyl and nitrile group on the side chain, are listed. Specific examples include a film of resin composition containing alternate copolymer including isobutylene and N-methyl maleimide, and acrylonitrile-styrene copolymer. The film may be a film formed by a mixed extrudate of the resin composition. Such films have small retardation, and small photoelastic coefficient, and thus drawbacks such as unevenness due to strain of the polarizing plate can be resolved, and furthermore, excellent humidification durability is obtained since the moisture permeability is small.

Furthermore, the polarizer protective film is preferably not colored as much as possible. Therefore, a protective film in which the retardation value in the film thickness direction expressed as $Rth=[(nx+ny)/2-nz] \cdot d$ (wherein nx, ny are main index of refraction in film surface, nz is an index of refraction in the film thickness direction, and d is film thickness) is between −90 nm and +90 nm is preferably used. The coloring (optical coloring) of the polarizing plate caused by the polarizer protective film can be substantially resolved by using that whose retardation value (Rth) in the thickness direction is between −90 nm and +90 nm. The retardation value (Rth) in the thickness direction is more preferably between −80 nm and +80 nm, and particularly between −70 nm and +70 nm.

From the standpoints of polarizing characteristics and durability, acetate resin such as triacetyl cellulose is preferable, and in particular, triacetyl cellulose film whose surface is saponification processed with alkali etc. is preferable. When arranging the polarizer protective film on both sides of the polarizer, the polarizer protective film including different polymers may be used on the front and the back. The thickness of the polarizer protective film is arbitrary, but is generally less than or equal to 500 μm, preferably between 1 to 300 μm, and more preferably between 5 and 200 μm in an aim of thinning the polarizing plate.

The retardation layer to be layered on the polarizing plate merely needs to be an optical layer having retardation, and examples of the retardation layer include a polymer-applied dry layer, orientation fixed layer of liquid crystal molecules, and polymer film such as retardation plate or temporarily attached film laminated via a bond layer. The present invention is, in particular, preferably applied to inspection of a layered film in which the retardation layer having large retardation variation in the film surface is layered, wherein the retardation layer having large retardation variation includes a separator temporarily attached to the polarizing plate via an adhesive, or a polarizing plate protective film layered with the adhesive and temporarily attached to protect the surface of the polarizing plate. The film temporarily attached to the polarizing plate is generally used at the time of conveyance, and is a film that will be stripped when mounting the polarizing plate, and thus, the retardation variation in the film plate is not as strictly controlled. Thus, the defect inspection of the polarizing plate layered with the temporarily attached film is relatively difficult.

The retardation orientation can be indicated with orientation angle variation of molecules. The orientation angle variation is an index representing the extent of shift from the desired orientation angle of the molecules for controlling the retardation of the retardation layer, but the present invention can be preferably applied even to the layered film having the retardation layer in which the orientation angle variation is greater than or equal to 6°, and inspection of satisfactory accuracy can be performed. The orientation angle variation is obtained by measuring the orientation angle at about three to six points equally in the width direction of the film, and obtaining the difference between the maximum value and the minimum value, wherein the orientation angle can be measured with a commercially available retardation measurement apparatus such as KOBRA-21ADH manufactured by Oji Keisoku Co.

The polarizer protective film may be subjected to hard coating process, antireflection process, and process targeting prevention of sticking, diffusion, anti-glare and the like. The hard coating process is performed in an aim of preventing scratches on the surface of the polarizing plate, and may be formed with a method for adding a curing membrane excellent in hardness, slipping property, and the like by an appropriate ultraviolet curable resin of silicone series etc. to the surface of the transparent protective film.

The antireflection process is performed in an aim of preventing reflection of outside light at the surface of the polarizing plate and is achieved by forming an antireflection film in accordance with the prior art. The sticking prevention is performed in an aim of preventing close attachment to an adjacent layer, and the anti-glare process is performed in an aim of preventing the outside light from reflecting at the surface of the polarizing plate and inhibiting the visibility of the transmitted light of the polarizing plate, and they are achieved by providing a microscopic concave-convex structure on the surface of the transparent protective film with an appropriate method such as coarse surface manner by sandblast manner, emboss processing manner, and the like or a manner of compounding transparent fine particles, and the like.

The layered film according to the present invention is used as an optical film by layering various optical layers in practical use. The optical layer is not particularly limited, but includes a method for performing hard coating process, antireflection process, and surface treatment in an aim of preventing sticking or diffusion and antiglare, or layering an orientation liquid crystal layer in an aim of compensating viewing angle etc. with respect to a surface (surface not arranged with the adhesive application layer) on which the polarizer of the transparent protective film is not adhered. The film in which one or two and more optical films used for forming the liquid crystal display device etc. such as reflection plate, semi-transmissive plate, retardation plate (including wavelength plate (λ plate) such as ½ and ¼), viewing angle compensation film, and the like are laminated may be used. In particular, if the sheet-form product is the polarizing plate, it is preferably applied as reflective polarizing plate or semi-transmissive polarizing plate formed by layering the reflective plate or the semi-transmissive reflection plate; elliptical polarizing plate or circular polarizing plate formed by layering the retardation plate; wide viewing angle polarizing plate formed by layering the viewing angle compensation layer or the viewing angle compensation film; or polarizing plate formed by layering luminance enhancement film.

The reflective polarizing plate has a reflection layer arranged on the polarizing plate, and is used to form a liquid crystal display device etc. of a type for displaying by reflecting the incident light from the viewing side (display side), wherein it has advantages that incorporation of a light source such as backlight can be omitted and that thinning of liquid crystal display device can be achieved. The reflective polarizing plate is formed with an appropriate manner such as a manner for attaching a reflection layer made of metal etc. on one side of the polarizing plate via the transparent protective layer etc. if necessary.

The semi-transmissive polarizing plate can be obtained as a reflection layer of semi-transmissive type such as half mirror for reflecting and transmitting the light by the reflection layer. The semi-transmissive polarizing plate is normally arranged on the back side of the liquid crystal cell, and can form a liquid crystal display device etc. of a type of displaying the image by reflecting the incident light from the viewing side (display side) when using the liquid crystal display device etc. in a relatively bright atmosphere, and displaying the image by using an incorporating light source such as backlight incorporated on the back side of the semi-transmissive polarizing plate when using the device in a relatively dark atmosphere. In other words, the semi-transmissive polarizing plate is useful for forming the liquid crystal display device etc. of a type that can save energy in use of light source such as back light under a bright atmosphere, and that can use an incorporating light even under a relatively dark atmosphere.

The elliptical polarizing plate or the circular polarizing plate formed by further layering the retardation plate on the polarizing plate will now be described. The retardation plate etc. is used when changing the linear polarized light to elliptical polarized light or circular polarized light, changing the elliptical polarized light or circular polarized light to linear polarized light, or changing the polarizing direction of the linear polarized light. In particular, a so-called ¼ wavelength plate (also referred to as λ/4 plate) is used as the retardation plate for changing the linear polarized light to circular polarized light or changing the circular polarized light to linear polarized light. The ½ wavelength plate (also referred to as λ/2 plate) is normally used when changing the polarizing direction of the linear polarized light.

The elliptical polarizing plate is effectively used to compensate (prevent) coloring (blue or black) caused by birefringence of the liquid crystal layer of the super twist nematic (STN) liquid crystal display device, and displaying in black and white without color. Furthermore, that in which a three-dimensional refraction index is controlled is preferable in that coloring that occurs when viewing the screen of the liquid crystal display device from a diagonal direction can also be compensated (prevented). The circular polarizing plate is effectively used when adjusting the color tone of the image of the reflection type liquid crystal display device in which the image is color displayed, and also has an antireflection function.

The retardation plate includes a birefringence film formed by uniaxial or biaxial stretch processing a polymer raw material, an orientation film of a liquid crystal polymer, a film in which the orientation layer of the liquid crystal polymer is supported by a film, and the like. The stretching process is performed with a roll stretching method, long gap stretching method, tentar stretching method, tubular stretching method, and the like. The stretching magnification is generally about 1.1 to 3 times in the uniaxial stretching. The thickness of the retardation plate is also not particularly limited, but is generally between 10 and 200 μm, and preferably between 20 and 100 μm.

The polymer material includes polyvinyl alcohol, polyvinyl butyral, polymethyl vinyl ether, polyhydroxyethyl acrylate, hydroxyethyl cellulose, hydroxypropyl cellulose, methyl cellulose, polycarbonate, polyarylate, polysulfone, polyethylene telephtalate, polyethylene naphtalate, polyether sulfone, polyphenyl sulfide, polyphenylene oxide, polyaryl sulfone, polyvinyl alcohol, polyamide, polyimide, polyolefin, polyvinyl chloride, cellulose polymer, or various copolymers of binary series and ternary series, graft copolymer, blended article of the above, and the like. The polymer raw material becomes the orientated object (stretched film) by stretching and the like.

The liquid crystal polymer includes various types of principle chain type or side chain type in which the conjugated linear atom group (mesogen) that provides liquid crystal orientation is introduced to the principle chain or the side chain of the polymer. Specific examples of the liquid crystal polymer of principle chain type include polyester liquid crystal polymer, discotheque polymer, colesteric polymer and the like of nematic orientation having a structure in which the mesogenic group is bonded at the spacer part that provides bendability. Specific examples of the liquid crystal polymer of side chain type include those which include a mesogen part including a para substitution annular compound unit that provides nematic orientation via a spacer part having polysiloxane, polyacrylate, polymethacrylate, or polymalonate as the principle chain framework and conjugate atomic group as the side chain. The liquid crystal polymers are obtained by developing and heat treating a solution of liquid crystal polymer on the orientation processing surface such as that in which the surface of the thin film of polyimide, polyvinyl alcohol etc. formed on the glass substrate is subjected to rubbing process, and that in which silicon oxide is oblique vapor deposited.

The retardation plate may have an appropriate retardation depending on the usage purpose such as purpose of compensating coloring, viewing angle, and the like by birefringence of various wavelength plates and liquid crystal layer, or may have optical characteristics such as retardation controlled by layering two or more types of retardation plates.

The polarizing plate in which the polarizing plate and the luminance enhancement film are laminated is normally used by being arranged on the back side of the liquid crystal cell. The luminance enhancement film has characteristics in reflecting linear polarized light of a predetermined polarizing axis or circular polarized light of a predetermined direction when natural light enters by back light of the liquid crystal display device etc. or by reflection from the back side, and transmitting other lights, wherein the polarizing plate in which the luminance enhancement film is layered with the polarizing plate transmits the light from the light source such as the back light to obtain the transmitted light of a predetermined polarization state, and reflects lights other than in the predetermined polarization state without transmitting. The light reflected by the luminance enhancement film surface is inverted via a reflection layer etc. arranged further on the rear side thereof to again enter the luminance enhancement film, wherein some or all of the lights are transmitted as light of a predetermined polarization state to increase the light quantity to be transmitted through the luminance enhancement film, and the polarized light less likely to be absorbed by the polarizer is supplied to increase the light quantity that can be used in the liquid crystal display image display etc. thereby enhancing luminance.

The layered film of the present invention may be formed by layering the polarizing plate or two layers of or three or more layers of optical layers as in a polarization separation polarizing plate. Therefore, the reflection type elliptical polarizing plate, the semi-transmissive type elliptical polarizing plate, and the like in which the reflective polarizing plate or the semi-transmissive polarizing plate is combined with the retardation plate may be used.

The optical film in which the optical layer is layered on the polarizing plate may be formed with a manner of sequential and separate layering in the fabrication process of the liquid crystal display device and the like, but the optical film obtained by being layered in advance is advantageous in that it is excellent in stability of the quality, assembly work, etc. and enhances the fabrication step of the liquid crystal display device, and the like. An appropriate adhering means such as adhesive layer may be used for layering. In adhering the above described polarizing plate and another optical layer, the optical axes thereof have an appropriate arrangement angle depending on the target retardation characteristics, and the like.

An adhesive layer for adhering with another member such as liquid crystal cell may be arranged on the polarizing plate according to the present invention or the layered optical member. The adhesive layer is not particularly limited, and may be formed with an appropriate adhesive in accordance with the prior art such as acryl series. In view of preventing foaming phenomenon and stripping phenomenon by moisture absorption, lowering of optical characteristics by thermal expansion difference, preventing warp of the liquid crystal cell, and furthermore, forming the image display device having high quality and excellent in durability, the adhesive layer having low moisture absorptivity and excellent in heat resistance is preferable. The adhesive layer containing fine particles and providing light diffusability may be used. The adhesive layer merely needs to be arranged on the required surface if necessary, and the adhesive layer may be arranged on one side or on both sides of the protective film with respect to the polarizing plate including the polarizer and the protective film.

Until provided for practical use, the separator is temporarily attached and covered on the exposure surface of the adhesive layer to prevent pollution etc. Thus, contact to the adhesive layer in the usual handling state is prevented. The separator may be appropriate one obtained in accordance with the prior art, having easy stripping performance and translucent performance, such as that obtained by performing coating process on a translucent plastic film such as polyester and polyethylene telephtalate with an appropriate stripping agent such as silicone or long chain alkyl, fluorine or molybdenum sulfide. The easy stripping protective film in which the bonding layer is layered on the translucent plastic film may be temporarily attached to the surface of the layered film without the adhesive layer, thereby protecting the layered film.

In the present invention, ultraviolet absorption ability may be provided to the polarizer, the transparent protective film, the optical film, or the like forming the polarizing plate, and each layer such as adhesive layer with manners such as a manner of processing with ultraviolet absorber such as ester salicylate compound, benzophenol compound, benzotriazole compound, cyanoacrylate compound, nickel complex salt compound, and the like.

The layered film according to the present invention is preferably used in forming a liquid crystal display device, an organic EL display device, and an image display device such as PDP.

The polarizing plate or the optical film of the present invention can be preferably used for forming various devices such as a liquid crystal display device. The liquid crystal display device is formed in accordance with the prior art. In other words, the liquid crystal display device is generally formed by appropriately assembling the liquid crystal cell, the polarizing plate or the optical film, and optional components of the illumination system etc., and incorporating a drive circuit, but is not particularly limited in the present invention other than that the polarizing plate or the optical film according to the present invention is used, and is in accordance with the prior art. With regards to the liquid crystal cell, an arbitrary type such as TN type, STN type, π type, or the like may be used.

The liquid crystal display device in which the polarizing plate or the optical film is arranged on one side or both sides of the liquid crystal cell, or an appropriate liquid crystal display device using a backlight or a reflection plate in the illumination system may be formed. In this case, the polarizing plate or the optical film of the present invention may be arranged on one side or both sides of the liquid crystal cell. When arranging the polarizing plate or the optical film on both sides, they may be the same or different. Furthermore, when forming the liquid crystal display device, an appropriate component such as a diffusion plate, an antiglare layer, an antireflection film, a protective plate, a prism array, a lens array sheet, a light diffusion plate, a backlight, or the like may be arranged at an appropriate position for one or two or more layers.

An organic electroluminescence device (organic EL display device) will now be described. Generally, the organic EL display device forms a light emitting body (organic electroluminescence light emitting body) by layering in order a transparent electrode, an organic light emitting layer, and a metal electrode on a transparent substrate. The organic light emitting layer is known as a layered body of various organic thin films, and a configuration of various combinations such as a layered body including a hole injection layer containing triphenylamine derivative etc., and a light emitting layer containing fluorescence organic solid of anthracene etc.; layered body including such light emitting layer and electron injection layer containing perylene derivative; and layered body including such hole injection layer, light emitting layer, and electron injection layer may be adopted.

In the organic EL display device including the organic electroluminescence light emitting body having a transparent electrode on the front surface side of the organic light emitting layer that emits light by voltage application and a metal electrode on the back surface side of the organic light emitting layer, the polarizing plate is arranged on the front surface side of the transparent electrode, and the retardation plate is arranged between the transparent electrode and the polarizing plate.

Since the retardation plate and the polarizing plate act to polarize the light entered from the outside and reflected by the metal electrode, they have an effect of preventing the mirror finished surface of the metal electrode from becoming visible from the outside by such polarization action. In particular, the mirror finished surface of the metal electrode can be completely shielded by forming the retardation plate with the ¼ wavelength plate, and adjusting the angle formed in the polarizing direction by the polarizing plate and the retardation plate to π/4.

The layered film according to the present invention can be preferably used for forming various devices such as a liquid crystal display device. The liquid crystal display device is formed with an appropriate configuration in accordance with the prior art of transmissive type, reflective type, or transmissive-reflective type by arranging the layered film (e.g., polarizing plate) according to the present invention on one side or on both sides of the liquid crystal cell. Therefore, the liquid crystal cell forming the liquid crystal display device is arbitrary, and the liquid crystal cell of an appropriate type such as simple matrix drive type represented by a thin-film transistor may be used.

The invention claimed is:

1. A layered film fabrication method comprising the steps of fabricating a layered film by layering at least a polarizing plate and a retardation layer, and performing defect inspection of the fabricated layered film, wherein the defect inspection step includes the steps of:
  irradiating a light on the layered film from a light source arranged on one side of a film surface of the layered film;
  imaging a transmitted light image of the layered film by an imaging unit arranged on the other side of the film surface;
  detecting a defect existing in the layered film based on the transmitted light image imaged by the imaging unit; and
  adjusting a relative angle position of a polarizing axis of an inspection polarization filter arranged on a light path between the film surface and the imaging unit and a polarizing axis of the polarizing plate; and
the relative angle position adjustment of the polarization filter includes adjusting a relative angle position x of the polarization filter in a range of $0° < x \leq 15°$ so that a light quantity of a visible light entered to the imaging unit becomes a minimum value.

2. A defect detection method of a layered film in which at least a polarizing plate and a retardation layer are layered, the method comprising the steps of:
  irradiating a light on the layered film from a light source arranged on one side of a film surface of the layered film;
  imaging a transmitted light image of the layered film by an imaging unit arranged on the other side of the film surface;
  detecting a defect existing in the layered film based on the transmitted light image imaged by the imaging unit; and adjusting a relative angle position of a polarizing axis of an inspection polarization filter arranged on a light path between the film surface and the imaging unit and a polarizing axis of the polarizing plate; wherein the relative angle position adjustment of the polarization filter includes adjusting a relative angle position x of the polarization filter in a range of $0°<x\leqq 15°$ so that a light quantity of a visible light entered to the imaging unit becomes a minimum value.

3. The layered film defect detection method according to claim 2, wherein the retardation layer has an orientation angle variation in plane of greater than or equal to 6°.

4. A defect detection device of a layered film in which at least a polarizing plate and a retardation layer are layered, the device comprising:
   a light source arranged on one side of a film surface of the layered film and irradiating a light on the layered film;
   an imaging unit arranged on the other side of the film surface and imaging a transmitted light image of the layered film;
   an inspection polarization filter arranged on a light path between the film surface and the imaging unit;
   a defect detection unit for detecting a defect existing in the layered film based on the transmitted light image imaged by the imaging unit; and
   an optical axis adjustment unit for adjusting a relative angle position of a polarizing axis of the polarization filter and a polarizing axis of the polarizing plate; wherein the optical axis adjustment unit adjusts a relative angle position x of the polarization filter in a range of $0°<x\leqq 15°$ so that a light quantity of a visible light entered to the imaging unit becomes a minimum value.

5. The layered film defect detection device according to claim 4, wherein the optical axis adjustment unit adjusts the relative angle position by rotating the polarization filter.

6. The layered film defect detection device according to claim 4, wherein the optical axis adjustment unit arranges one polarization filter selected from a plurality of polarization filters having a polarizing axis set in different directions on the light path.

7. A layered film inspected by the defect detection device according to any one of claims 4.

8. A layered film in which at least one optical layer is layered on the layered film according to claim 7.

9. An image display device including the layered film according to claim 7.

* * * * *